US006284517B1

(12) United States Patent
Restaino

(10) Patent No.: US 6,284,517 B1
(45) Date of Patent: Sep. 4, 2001

(54) **PLATING MEDIA FOR THE PRESUMPTIVE IDENTIFICATION OF *BACILLUS CEREUS* AND *BACILLUS THURINGIENSIS***

(76) Inventor: Lawrence Restaino, 43 W. 513 Tall Oaks Trail, Elburn, IL (US) 60119

( * ) Notice: Subject to any disclaimer, the term of this patent is extended or adjusted under 35 U.S.C. 154(b) by 0 days.

(21) Appl. No.: 09/321,529

(22) Filed: May 28, 1999

(51) Int. Cl.[7] .............................. C12N 1/00; C12N 1/12; C12N 1/20

(52) U.S. Cl. .................................... 435/252.4; 435/252.1; 435/832; 435/252.5; 435/253.6; 435/834

(58) Field of Search ........................... 435/252.1, 252.31, 435/252.4, 525.5, 253.6, 834, 832

(56) References Cited

U.S. PATENT DOCUMENTS 5,063,055 * 11/1991 Burges et al. ......................... 424/93
5,523,214 * 6/1996 Horn ...................................... 435/52
5,783,561 * 7/1998 Horwitz et al. ........................ 514/12

OTHER PUBLICATIONS

Restaino et al., Isolation and detection of *Listeria monocytogenes* using fluorogenic and chromogenic substrates for phosphatidylinositol–specific phospholipase C. Journal of Food Protection. vol. 62, No. 3, pp. 244–251. See abstract only, Mar. 1999.*

* cited by examiner

*Primary Examiner*—Deborah K. Ware
(74) *Attorney, Agent, or Firm*—Marshall A. Burmeister

(57) ABSTRACT

An isolation plating medium and mixture for simultaneously identifying Bacillus species are disclosed. The specific bacilli identified are *Bacillus thuringiensis* and *Bacillus cereus.* The medium and mixture contain nutrients, inhibitory ingredients to inhibit the growth of other bacteria yeast and molds and a chromogenic substrate. The substrate changes color in response to the production of phosphatidylinositol-specific phospholipase C for the identification of the bacteria.

14 Claims, No Drawings

PLATING MEDIA FOR THE PRESUMPTIVE IDENTIFICATION OF *BACILLUS CEREUS* AND *BACILLUS THURINGIENSIS*

BACKGROUND OF THE INVENTION

The present invention relates to the presumptive identification of bacteria, and in particular to the presumptive identification the microorganisms *Bacillus cereus* and *Bacillus thuringiensis*.

Chapter 35 of the *Compendium of Methods for the Microbiological Examination of Foods*, American Public Health Association, 1992, questions whether *Bacillus thuringiensis* is a separate species or a variety of *Bacillus cereus* because of the cultural similarity of the microorganisms. Here they are considered separate species. *Bacillus cereus* and *Bacillus thuringiensis* are found on a variety of foods, and have been implicated in food poisoning of humans. For this reason and the fact that they are similar in characteristics, it is desirable to consider both in the process of making a presumptive identification from a mixed sample.

The *Compendium of Methods for the Microbiological Examination of Foods*, supra, describes the Kim-Goepfert agar and the mannitol yolk polymyxin agar for presumptive identification of *Bacillus cereus* from a mixed sample, and points out that these plating media are not 100% selective and may be difficult to interpret.

The paper entitled Phosphatidylinositol-Specific Phospholipases C from *Bacillus cereus* and *Bacillus thuringiensis* by O. H. Griffith, J. J. Volwerk and A. Kuppe, Methods in Enzymology, Vol. 197 Academic Press, Inc. 1991, investigates the production of the enzyme Phosphatidylinositol-Specific Phospholipases C produced by both *Bacillus cereus* and *Bacillus thuringiensis*. M. Ryan, J. Huang, O. H. Griffith, J. F. W. Keana, and J. J. Volwerk describe detection of Phosphatidylinositol-Specific Phospholipase C produced by *Bacillus cereus* and *Bacillus thuringiensis* with a chemiluminescent substrate in the paper entitled A Chemiluminescent Substrate for the Detection of Phosphatidylinositol-Specific Phospholipase C, Analytical Biochemistry, Vol. 214, pages 548–556 (1993). In a paper entitled Isolation and Detection of Listeria monocytogenes Using Fluorogenic and Chromogenic Substrates for Phosphatidylinositol-Specific Phospholipase C, by L. Restaino (the present inventor), E. W. Frampton, R. M. Irbe, Günter Schabert, and Hans Spitz, Journal of Food Protection, Vol 62, No. 3, 1999, Pages 244–251, a chromogenic substrate is disclosed for Listeria responsive to the production of phosphatidylinositol-specific phospholipase C.

SUMMARY OF THE INVENTION

It is a principle object of the present invention to provide a plating medium with a chromogenic substrate for the presumptive identification of *Bacillus cereus* and *Bacillus thuringiensis* from a mixed sample, and to identify both species of Bacillus symultaneosly.

The inventor has recognized that when disposed in a growth medium both *Bacillus cereus* and *Bacillus thuringiensis* secrete the enzyme phosphatidylinositol-specific phospholipase C into the growth medium. It is an object of the present invention to provide a plating medium for the presumptive identification of *Bacillus cereus* and *Bacillus thuringiensis* that has a phosphatidylinositol-specific phospholipase C responsive chromogenic substrate, thus providing a medium that simultaneously responds to both *Bacillus cereus* and *Bacillus thuringiensis* bacteria. The inventor recognized that the chromogenic substrate 5-bromo-4-chloro-3-indoxyl-myo-inositol-1-phosphate is responsive to Phosphatidylinositol-Specific Phospholipase C secreted by *Bacillus cereus* and *Bacillus thuringiensis* from his work on Listeria reported in the paper entitled Isolation and Detection of Listeria monocytogenes Using Fluorogenic and Chromogenic Substrates for Phosphatidylinositol-Specific Phospholipase C, supra, and it is an object of the present invention to provide a plating medium utilizing this chromogen for the presumptive identification of *Bacillus cereus* and *Bacillus thuringiensis*.

The plating medium, according to the present invention, comprises (1) a nutrient media that promotes the growth of *Bacillus cereus* and *Bacillus thuringiensis* under conditions promoting incubation, (2) at least one ingriedient that resusitates damaged Bacillus cells under incubation, (3) at least one ingredient that promotes generation of *Bacillus cereus* spores under incubation, (4) at least one ingredient that under incubation inhibits the growth of Bacillus bacteria other than *Bacillus cereus* and *Bacillus thuringiensis* and other related bacteria, (5) at least one ingredient that inhibits the growth of yeast and molds under incubation, (6) the substrate 5-bromo-4-chloro-3-indoxyl-myo-inositol-1-phosphate, (7) at least one ingredient that promotes the expression of the enzyme to react with the substrate, and (8) at least one ingredient that solidifies the mixture.

DETAILED DESCRIPTION OF THE INVENTION

It is necessary that the Bacillus bacteria consume nutrients and grow in order for the bacteria to secrete enzymes. Hence the plating medium must have a rich nutrient base. In order to promote the growth of the various strains of Bacillus bacteria, the plating media of the present invention include one or more of the ingredients proteose peptone, LAB LEMCO (meat extract) powder, and yeast extract. In the preferred medium described throughout this specification, all three of these ingredients are in the plating medium and form the nutrient base.

The preferred plating medium includes sodium pyruvate to facilitate the resuscitation of damaged Bacillus cells, and magnesium sulfate to promote germination of *Bacillus cereus* spores.

In any plating medium, the growth of cells of bacteria other than the bacteria of interest complicates or completely frustrates reading of the plate, and hence it is desirable or necessary to inhibit the growth of species other than the one or ones of interest. The media of the present invention must suppress all strains of Bacillus other than *Bacillus cereus* and *Bacillus thuringiensis* and related bacteria. For this purpose, the media of the present invention contain one or more of the ingredients lithium chloride, ceftazidime, polymixin B sulfate, the third and fourth generation of cephalosporins, and moxactan. The preferred plating medium contains lithium chloride, ceftazidime, and polymixin B sulfate.

The preferred medium contains cycloheximide to inhibit the growth of yeast and molds. The chromogenic substrate that changes color responsive to the presence of phosphatidylinositol-specific phospholipase C in the preferred medium is 5-bromo-4-chloro-3-indoxyl-myo-inositol-1-phosphate.

Ingredients that permit the activation of the enzyme phosphatidylinositol-specific phospholipase C in the plating media are bovine serum and powdered silicates. In the preferred embodiment, this ingredient is bovine serum.

The plating media also contains at least one ingredient to maintain the pH of the medium in a suitable range, namely, potassium phosphate (monobasic) and/or sodium phosphate (dibasic). In the preferred embodiment, both potassium phosphate and sodium phosphate are used in the media.

An ingredient must be added to the mixture to solidify the mixture. In the preferred composition, this ingredient is agar. The formula for the preferred embodiment of the plating media is set forth in Table 1.

TABLE 1

| CHEMICAL | SUPPLIER | GRAMS/LITER |
|---|---|---|
| Proteose peptone | Difco | 10.00 |
| LAB LEMCO powder | Oxoid | 5.00 |
| Yeast extract | Difco | 6.00 |
| Sodium pyruvate | Biosynth | 10.00 |
| Potassium phosphate (monobasic} | | 0.24 |
| Sodium phosphate (dibasic) | | 2.50 |
| Magnesium sulfate Anhydrous | | 0.06 |
| Cycloheximide | | 0.20 |
| Lithium chloride | Sigma | 2.00 |
| Agar | Difco | 15.00 |
| Bovine Serum 82-067 | Bayer | 4.20 |
| Ceftazidime | Glaxo Wellcome | Sufficient to suppress Bacillus other than *B. cereus* and *B. thuringiensis* |
| 5-bromo-4-chloro-3-indoxyl-myo-inositol-1-phosphate. | Biosynth | 0.35 |
| Polymixin B sulfate | Sigma | 0.013 |

Prior to the preparation of the plating medium, the ingredients are admixed into four components. The first component includes proteose peptone, potassium phosphate (monobasic), LAB LEMCO powder, and cycloheximide. The second component contains yeast extract, sodium pyruvate, and magnesium sulfate. The third component contains sodium phosphate (dibasic), lithium chloride, and agar. The fourth component is the remaining ingredients, each of which is maintained separately under its prescribed stage conditions until the plating medium is to be produced.

The composition is prepared by admixing the three components set forth above, under sterile conditions, and each of the first three components is admixed. Thereafter, one at a time, the remaining four components, 5-bromo-4-chloro-3-indoxyl-myo-inositol-1-phosphate, bovine serum, ceftazidine, and polymixin B sulfate, are added to the mixture. The composition is then placed in petri dishes and stored under proper conditions overnight.

EXAMPLE I

The bacterial strains indicated in Table 2 were applied to the petri dishes referred to above, and incubated at 35 degrees Celsius for a period of 24 hours. Thereafter, the surfaces of the platting media in the petri dishes were observed, and produced the following results.

TABLE 2

| Bacteria | Number of Strains | Colonial Morphology |
|---|---|---|
| *Bacillus cereus* | 8 | Turquoise flat dull colonies; 2–7 mm with and without turquoise halos |
| *Bacillus thuringiensis* | 3 | Turquoise flat dull colonies; 2–8 mm with and without turquoise halos |
| *Bacillus circulans* | 1 | White domed dull colonies; 1–2 mm |
| *Bacillus megaterium* | 2 | No growth |
| *Bacillus licheniformis* | 3 | No growth |
| *Bacillus subtilis*, *Bacillus brevis*, *Bacillus lentus*, *Bacillus pumilus*, *Bacillus spaericus*, *PaeniBacillus macerans*, *PaeniBacillus polymyxa*, *Bacillus mycoides*, and *Bacillus insolitus* | 1 strain each | No growth |
| *Listeria monocytogenes* | 3 | No growth to turquoise domed colonies; pinpoint to <1 mm |
| *Listeria ivanovii* | 1 | Turquoise domed colonies; pinpoint to <1 mm |
| *Listeria innocua*, *Listeria seeligeri*, and *Listeria welshimeri* | 1 strain each | White domed colonies; pinpoint to <1 mm |
| *Enterococcus faecium* | 4 | No growth to white domed colonies; pinpoint |
| *Enterococcus faecalis* | 2 | No growth to white domed colonies; pinpoint |
| *Enterococcus avium* | 3 | No growth |
| *Staphylococcus aureus* | 5 | No growth |
| Micrococcus sp., *Pediococcus cerevisiae*, *Staphylococcus epidermidis*, and *Staphylococcus saprophyticus* | 1 strain each | No growth |
| Gram negative species* | 7 | No growth |

*One strain each of *Pseudomonas aeruginosa*, *Escherichia coli*, *Enterobacter agglomerans*, *Salmonella derby*, *Salmonella typhimurium*, *Klebsiella pneumoniae*, and *Escherichia coli* 0157:H7.

From Table 2, it is clear that *Bacillus cereus* and *Bacillus thuringiensis* produce significantly large colonies on the plating medium and are further readily distinguishable by their turquoise color.

It should also be noted that of the Bacillus genus, only *Bacillus cereus* and *Bacillus thuringiensis* produce significant colonies on the preferred medium. Table 3 compares the phosphatidylinositol-specific phospholipase C production of Bacillus species.

TABLE 3

| SPECIES | ATCC NUMBERS | NUMBER OF STRAINS TESTED | ENZYME PRODUCTION |
|---|---|---|---|
| *Bacillus cereus* | 11778, 13061, 14549 and 21281 | 8 | + |
| *Bacillus thuringiensis* | 33680 and 39152 | 3 | + |
| *Bacillus circulans* | 4513 | 1 | – |
| *Bacillus megaterium* | 14581 | 2 | – |

TABLE 3-continued

| SPECIES | ATCC NUMBERS | NUMBER OF STRAINS TESTED | ENZYME PRODUCTION |
|---|---|---|---|
| *Bacillus licheniformis* | 10716 and 11946 | 3 | – |
| *Bacillus subtilis* | 37015 | 1 | – |
| *Bacillus brevis* | 8246 | 1 | – |
| *Bacillus pumilus* | 7061 | 1 | – |
| *Bacillus sphaericus* | 14577 | 1 | – |
| *Bacillus macerans* | 8244 | 1 | – |
| *Bacillus polymyxa* | 842 | 1 | – |
| *Bacillus mycoides* | — | 1 | – |
| *Bacillus insolitus* | 23299 | 1 | – |

Table 3 shows that the generally known species of Bacillus, except for *Bacillus cereus* and *Bacillus thuringiensis,* are not producers of phosphatidylinositol-specific phospholipase C, and accordingly these species will not produce colonies on the preferred plating medium.

Although variations in the plating medium of the preferred embodiment are set forth above, other variations will become apparent to those skilled in the art. It is therefore intended that this invention be not limited to the foregoing specification, but rather only to the appended claims

The invention claimed is:

1. Isolation plating medium for the simultaneous identification of *Bacillus cereus* and *Bacillus thuringiensis* consisting essentially of a mixture of (1) nutrients that promote growth of cells of *Bacillus cereus* and *Bacillus thuringiensis* under suitable environmental conditions for growth, (2) an ingredient that facilitates resuscitation of damaged *Bacillus cereus* and *Bacillus thuringiensis* cells under suitable environmental conditions for growth, (3) an ingredient that promotes germination of Bacillus spores under suitable environmental conditions for growth, (4) an ingredient that inhibits the growth of strains of related bacteria and Bacillus other than *Bacillus cereus* or *Bacillus thuringiensis* under suitable environmental conditions for growth, (5) an ingredient that inhibits the growth of yeast and molds, (6) a chromogenic substrate that changes color responsive to the presence of phosphatidylinositol-specific phospholipase C, and (7) an ingredient for thickening the mixture in sufficient quantity to solidify the mixture.

2. The medium of claim 1 wherein the nutrients that promote growth of said cells of *Bacillus cereus* and *Bacillus thuringiensis* consists of one or more members of the class proteose peptone, meat extract powder, and yeast extract.

3. The medium of claim 1 wherein the ingredient that facilitates resuscitation of damaged *Bacillus cereus* and *Bacillus thuringiensis* cells consists of sodium pyruvate.

4. The medium of claim 1 wherein the ingredient that promotes germination of Bacillus spores consists of magnesium sulfate.

5. The medium of claim 1 wherein the ingredient that inhibits the growth of strains of related bacteria and Bacillus other than *Bacillus cereus* or *Bacillus thuringiensis* consists of one or more members of the class lithium chloride, ceftazidime, polymixin B sulfate, third and fourth generation cephalosporins, and moxalactan.

6. The medium of claim 1 wherein the ingredient that inhibits the growth of yeast and molds consists of a member of the class cycloheximide.

7. The medium of claim 1 wherein the chromogenic substrate that changes color responsive to the presence of phosphatidylinositol-specific phospholipase C consists of 5-bromo-4-chloro-3-indoxyl-myo-inositol-1-phosphate.

8. The medium of claim 1 wherein the ingredient for thickening the mixture to solidify the mixture consists of agar.

9. The medium of claim 1 wherein the mixture includes potassium phosphate.

10. The medium of claim 1 wherein the mixture includes sodium phosphate.

11. A method of simultaneously making an identification of *Bacillus cereus* and *Bacillus thuringiensis* from a specimen containing mixed bacteria comprising the steps of applying the specimen to an isolation plating medium of claim 10, establishing and maintaining said isolation plating medium at a temperature to promote growth of *Bacillus cereus* and *Bacillus thuringiensis* for a period of time sufficient to grow colonies of the bacteria on the plating medium, and identifying the colonies on the plating medium by observing phosphatidylinositol-specific phospholipase C produced by the bacteria.

12. A method of simultaneously making an identification of *Bacillus cereus* and *Bacillus thuringiensis* from a specimen containing mixed bacteria comprising the steps of applying the specimen to an isolation plating medium of claim 1, establishing and maintaining said isolation plating medium at a temperature to promote growth of *Bacillus cereus* and *Bacillus thuringiensis* for a period of time sufficient to grow colonies of the bacteria on the plating medium, and identifying colonies on the plating medium by observing phosphatidylinositol-specific phospholipase C produced by the bacteria.

13. Isolation plating medium for the simultaneous identification of *Bacillus cereus* and *Bacillus thuringiensis* consisting essentially of a mixture of (1) nutrients that promote growth of cells of *Bacillus cereus* and *Bacillus thuringiensis* under suitable environmental conditions for growth consisting of proteose peptone, meat extract powder, and yeast extract, (2) an ingredient that facilitates resuscitation of damaged *Bacillus cereus* and *Bacillus thuringiensis* cells consisting of sodium pyruvate, (3) an ingredient that promotes germination of Bacillus spores consisting of magnesium sulfate, (4) an ingredient that inhibits the growth of related bacteria and strains of Bacillus other than *Bacillus cereus* or *Bacillus thuringiensis* under suitable environmental conditions for growth consisting of lithium chloride, ceftazidime and polymixin B sulfate, (5) an ingredient that inhibits the growth of yeast and molds consisting of cycloheximide, (6) a chromogenic substrate consisting of 5-bromo-4-chloro-3-indoxyl-myo-inositol-1-phosphate and that changes color responsive to the presence of phosphatidylinositol-specific phospholipase C, and (7) agar in sufficient quantity to solidify the mixture.

14. A mixture for the simultaneous identification of *Bacillus cereus* and *Bacillus thuringiensis* consisting essentially of (1) nutrients that promote growth of cells of *Bacillus cereus* and *Bacillus thuringiensis* under suitable environmental conditions for growth, (2) an ingredient that inhibits the growth of strains of related bacteria and Bacillus other than *Bacillus cereus* or *Bacillus thuringiensis* under suitable environmental conditions for growth, (3) an ingredient that inhibits the growth of yeast and molds, and (4) a chromogenic substrate that changes color responsive to the presence of phosphatidylinositol-specific phospholipase C.

* * * * *